United States Patent
Fernando et al.

(10) Patent No.: US 10,911,422 B2
(45) Date of Patent: Feb. 2, 2021

(54) DATA TRUST SCORE

(71) Applicant: Arm IP Limited, Cambridge (GB)

(72) Inventors: Joseph Prasanna Fernando, Woodinville, WA (US); Karthik Ranjan, Kirkland, WA (US)

(73) Assignee: Arm IP Limited, Cambridge (GB)

(*) Notice: Subject to any disclaimer, the term of this patent is extended or adjusted under 35 U.S.C. 154(b) by 147 days.

(21) Appl. No.: 16/012,753

(22) Filed: Jun. 19, 2018

(65) Prior Publication Data

US 2019/0386974 A1  Dec. 19, 2019

(51) Int. Cl.
*H04L 29/06* (2006.01)
*H04W 12/06* (2009.01)
*G16H 10/65* (2018.01)
*G16H 80/00* (2018.01)
*G16H 20/10* (2018.01)

(52) U.S. Cl.
CPC ............ *H04L 63/08* (2013.01); *H04W 12/06* (2013.01); *G16H 10/65* (2018.01); *G16H 20/10* (2018.01); *G16H 80/00* (2018.01)

(58) Field of Classification Search
CPC ....... H04L 63/08; H04W 12/06; G16H 20/10; G16H 80/00; G16H 10/65
USPC .......................................................... 726/3
See application file for complete search history.

(56) References Cited

U.S. PATENT DOCUMENTS

| | | | |
|---|---|---|---|
| 6,711,742 B1* | 3/2004 | Kishi | H04L 29/06027 725/111 |
| 10,135,834 B1* | 11/2018 | Galebach | H04L 63/102 |
| 2011/0319746 A1* | 12/2011 | Kochba | A61B 5/0507 600/407 |
| 2017/0180341 A1* | 6/2017 | Walker | H04L 63/08 |
| 2018/0069836 A1* | 3/2018 | Mandyam | H04L 63/0853 |

FOREIGN PATENT DOCUMENTS

WO    2016-178127 A1    11/2016

OTHER PUBLICATIONS https://www.arm.com/products/security-on-arm/trustzone (downloaded/accessed Jun. 19, 2018).

* cited by examiner

*Primary Examiner* — Kambiz Zand
*Assistant Examiner* — Aubrey H Wyszynski
(74) *Attorney, Agent, or Firm* — Pramudji Law Group PLLC; Ari Pramudji

(57) ABSTRACT

Various implementations described herein are directed to determining a multi-factor trust score. Data from one or more endpoint devices is received over a gateway. A trust score is determined based on a plurality of metrics. The plurality of metrics including at least: a first attestation process performed for the one or more endpoint devices, and a second attestation process performed for the gateway. The trust score is sent to an analytics server. The trust score is configured to be used by the analytics server to determine an alert and/or a command based on the trust score.

20 Claims, 14 Drawing Sheets

| Metric | Weight Formula | Points | Score |
|---|---|---|---|
| Device attestation | 2 | 100 | 200 |
| Gateway attestation | 2 | 100 | 200 |
| Identity | 1 | 100 | 100 |
| Attribution | 1 | 100 | 100 |
| Consent/Approval | 2 | 100 | 200 |
| Device security level | 1 | 100 | 100 |
| Gateway security level | 1 | 100 | 100 |
| Total Score (out of 1000 possible) | | | 1000 |

Figure 7

| Metric | Weight Formula | Points | Score |
|---|---|---|---|
| Device attestation | 2 | 75 | 150 |
| Gateway attestation | 2 | 75 | 150 |
| Identity | 1 | 75 | 75 |
| Attribution | 1 | 100 | 100 |
| Consent/Approval | 2 | 75 | 150 |
| Device security level | 1 | 75 | 75 |
| Gateway security level | 1 | 75 | 75 |
| Total Score (out of 1000 possible) | | | 775 |

| Metric | Weight Formula | Points | Score |
|---|---|---|---|
| Device attestation | 2 | 0 | 0 |
| Gateway attestation | 2 | 0 | 0 |
| Identity | 1 | 50 | 50 |
| Attribution | 1 | 50 | 50 |
| Consent/Approval | 2 | 50 | 100 |
| Device security level | 1 | 0 | 0 |
| Gateway security level | 1 | 25 | 75 |
| Total Score (out of 1000 possible) | | | 275 |

DATA TRUST SCORE

BACKGROUND

In the medical technology field, data generated for a patient must be handled with care since the consequences of acting on incorrect information can be fatal. There is a great variance in the level of trust that can be had in data arriving from different sources. The cause of this variance includes different factors, including: the type of device from which the data originated; the path taken by the data to arrive at the management provider; and the degree to which the patient/device user has validated the data.

BRIEF DESCRIPTION OF THE DRAWINGS

Implementations of various techniques are described herein with reference to the accompanying drawings. It should be understood, however, that the accompanying drawings illustrate only the various implementations described herein and are not meant to limit the scope of various techniques described herein.

FIG. 7 illustrates an example table that includes the plurality of metrics used to determine a trust score in accordance with implementations of various techniques described herein.

FIG. 10 illustrates an example table that includes the plurality of metrics used to determine a trust score in accordance with implementations of various techniques described herein.

FIG. 13 illustrates an example table that includes the plurality of metrics used to determine a trust score in accordance with implementations of various techniques described herein.

DETAILED DESCRIPTION

The present disclosure describes generating metrics, in the form of a multi-factor score. This multi-factor score is based on measures associated with a plurality of metrics, e.g., device type, data path, the degree of validation of the data, etc. Using the generated metrics, it is possible for a cloud management service to determine data provenance and the degree to which the data can be trusted. Based on these evaluations, e.g., the data provenance and the trust level of the data, the system can take actions that are appropriate to the level of trust in that data.

The multi-factor, e.g., trust, score may be determined from a variety of metrics, including, but not limited to, device attestation, gateway attestation, patient identity, attribution, patient consent/approval, device security level, and gateway security level. A subject, e.g., device, data path, software, software code section, protocol, of each metric is designated points within the metric based on a level of security provided by the subject. In one implementation, weights can be assigned to each metric to provide a weighted trust score.

Device attestation is an affirmation that the device, including the hardware and software, has not been tampered with and is genuine. A device attestation metric score is determined based on a result of the device attestation affirmation. Gateway attestation is an affirmation that the gateway, including the hardware and software, has not been tampered with and is genuine. A gateway attestation metric score is determined based on a result of the gateway attestation affirmation.

The ability to attest that neither the device nor the gateway has been tampered with provides a higher assurance of the validity of the data, i.e., increases the trustworthiness of the data. The device from which the data has been generated and the gateway through which the data has been transmitted may employ a number of security features. In particular, some security features may include hardware-based security, e.g., a hardware cryptography block, built into System on Chips (SoCs) to provide secure endpoints and a device root of trust (RoT). Security features may also include in-built biometrics. Device hardware features permit the device to attribute and secure the data from the time and point of acquisition. Gateway features may be applied to further permit the projection of the data and to provide additional trust assurances.

Hardware-based security may also be referred to as hardware-backed security. Devices and gateways employing hardware-backed security can be combined with a trusted boot and a trusted operating system. When combined, the devices, gateways, trusted boot and trusted operating system operate within a trusted execution environment (TEE). Applications running within the TEE may be referred to as trusted applications.

Figure 1:
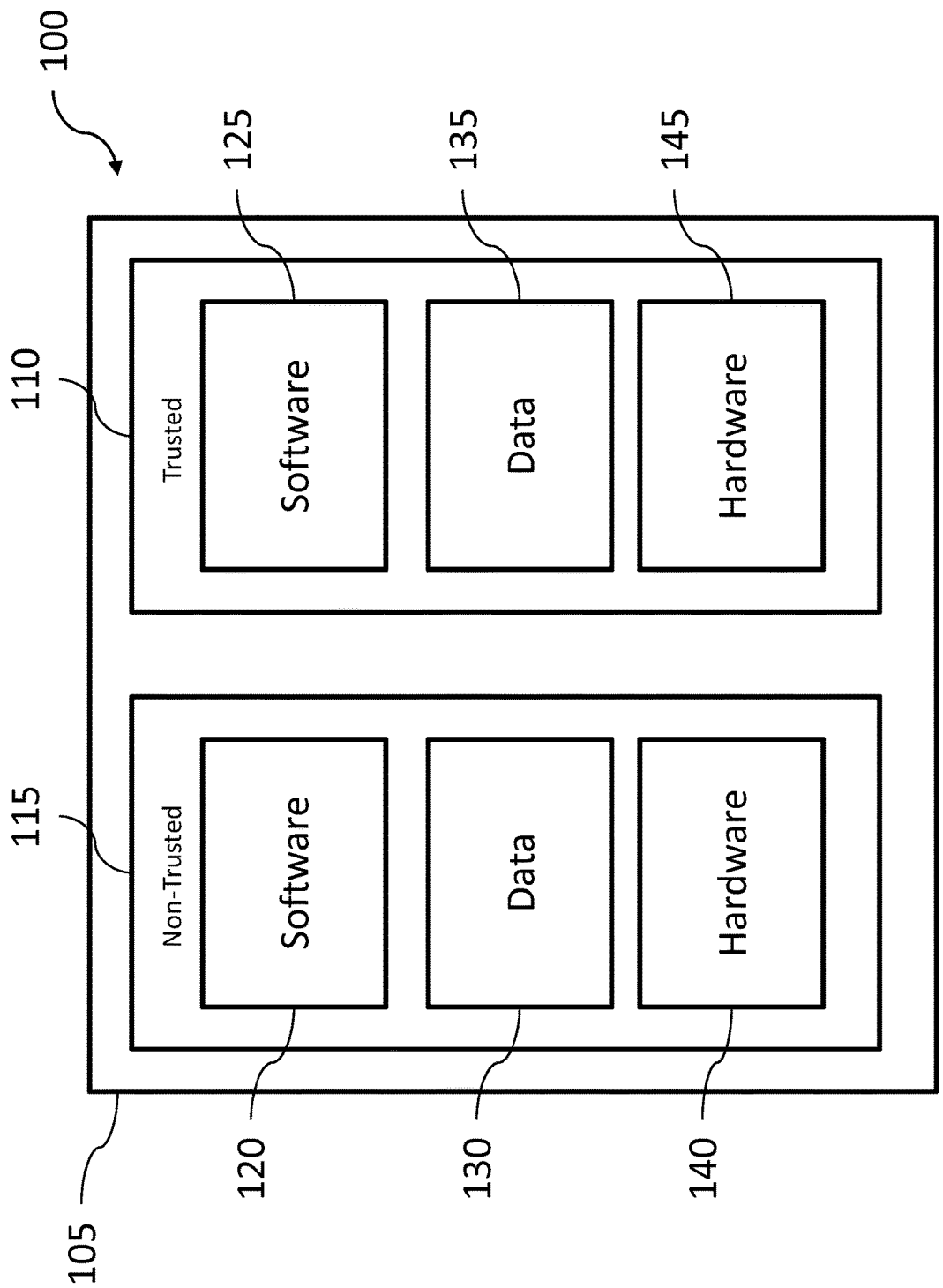
FIG. 1 illustrates an example of hardware-based security in accordance with implementations of various techniques described herein.

FIG. 1 illustrates an example of hardware-based security. FIG. 1 includes a system 100 employed by a device 105, e.g., an endpoint device or gateway device. The device 105 includes a secure, e.g., trusted, area 110 and a non-secure, e.g., non-trusted, area 115. The secure 110 and non-secure 115 areas include software 120, 125, data 130, 135, and hardware 140, 145. The secure area 110 and non-secure area 115 is hardware separated, with non-secure software blocked from accessing secure resources directly. Within the processor, software either resides in the secure area 110 or the non-secure area 115. Switching between the secure area 110 and the non-secure 115 area may be accomplished by security monitor software or core logic. The secure area 110 and non-secure area 115 may be extended to encompass memory, software, bus transactions, interrupts and peripherals within a SoC. Any part of the system 105 can be designed to be part of the secure area 110, including debug, peripherals, interrupts and memory. Using system 105, assets can be protected from software attacks and hardware attacks.

In one implementation, for a hardware root of trust (HRoT), the RoT resides in hardware 145. In one implementation, for a software root of trust (SRoT), the RoT resides in storage, e.g., data 135.

An identity metric increases trustworthiness of the data by performing an identity attestation process to determine an identity metric score based on an authentication status for identities of the participatory entities. The participatory entities may include a user, devices, a gateway, applications, services, and/or any other primary components that participated in the acquisition and/or handling of the data.

An attribution metric increases trustworthiness of the data by including an attribution score based on an analysis of available metadata associated with the data and/or transmission paths for the data. If metadata is available, the metadata is analyzed to determine a description of the data and/or a validity of the data. The attribution metric may also include the verifiability and discoverability of transmission paths for the data as a factor in the attribution metric score. The attribution metric score provides a measure of the traceability and auditability of the data.

A consent/approval metric increases the trustworthiness of the data by including a consent/approval score. The consent/approval score is based on a review and confirmation by a user that the data has been acquired using prescribed methodologies prior to providing consent for distribution. The consent/approval metric provides an indication of whether or not a user has attested that the data has been obtained through certain prescribed procedures and that the data belongs to the user.

A device security level metric increases the trustworthiness of the data by including a device security level score. The device security level score is based on the security capabilities of the device. Hardware-backed security, e.g., TEE, is deemed more secure and, thus, provides a higher device security level score than software-based security solutions.

A gateway security level metric increases the trustworthiness of the data by including a gateway security level score. The gateway security level score is based on the security capabilities of the gateway. Hardware-backed security, e.g., TEE, is deemed more secure and, thus, provides a higher gateway security level score than software-based security solutions.

Figure 2:
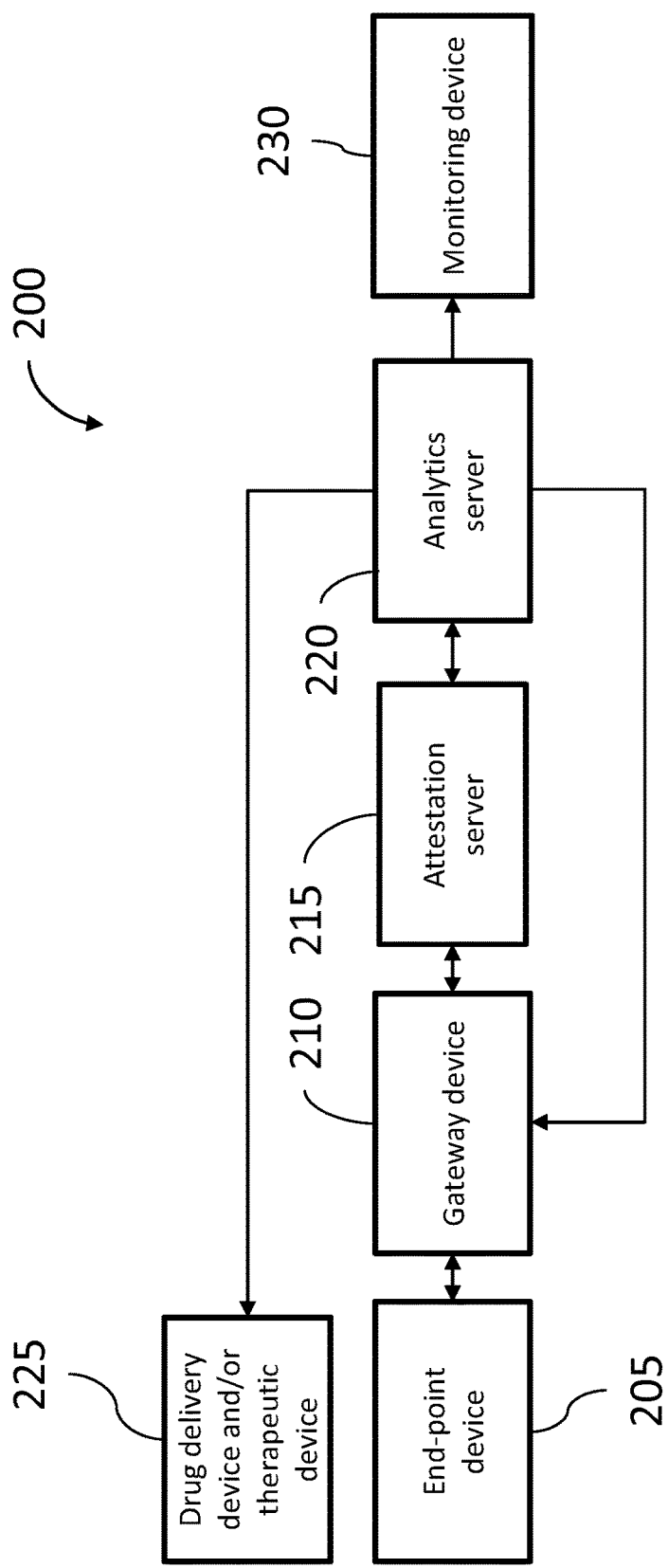
FIG. 2 illustrates an example system for implementing a multi-factor trust score in accordance with implementations of various techniques described herein.

FIG. 2 illustrates an example system for implementing a multi-factor trust score. System 200 includes an endpoint device 205, a gateway device 210, an attestation server 215, an analytics server 220, a drug delivery and/or therapeutic device 225, and an alert device 230.

The endpoint device 205 may be a medical testing and/or monitoring device. Endpoint device 205 may include any type of device that measures vital signs and/or performs medical tests.

Gateway device 210 may be at least one of: a mobile telephone; a wireless mobile device; a smart phone; a tablet; a phablet; a smart watch; a wearable computer; a personal computer; a desktop computer; a laptop computer; a personal digital assistant (PDA); etc. This list is exemplary only and should not be considered as limiting. Any suitable client computing device for implementing the gateway device 210 may be used.

Endpoint devices employing a sufficient RoT are able to safely store credentials and present these credentials to a device that is performing the attestation. Different technologies provide varying degrees of security—hence leading to different trust scores, and differences in how well the RoT is safeguarded. Endpoint devices exhibiting higher trust scores are able to prevent cloning, replay, and other types of attacks.

Gateway devices handle endpoint medical device attestation and data in transit from the sensor, e.g., endpoint, to the cloud, e.g., a cloud-based attestation server and a cloud-based analytics server. In terms of decrypting data from the end sensor, certain security feature products can be used to ensure isolated decryption of data on the gateway/phone and validation by the end user, therefore adding to the total provenance of the data score.

Attestation server 215 uses metrics to determine a trust score based on the capabilities of the endpoint device 205 and the gateway device 210. Based on the determined trust score, which is based on a plurality of metrics, the attestation server 215 determines what kind of trust can be accorded to the system and what kind of messages can be sent down, e.g., to devices 210, 225, 230.

With respect to endpoint device 205, the attestation server 215 communicates with the endpoint device 205 and includes a mechanism that prompts the endpoint device 205 to prove that it is a particular type of device and has certain characteristics, e.g., RoT, hardware-backed security, software encryption, etc. The attestation mechanism provided may be a software attestation, a hardware attestation or some combination of software attestation and hardware attestation. The endpoint device 205 is then assigned a score by the attestation server 215.

With respect to gateway device 210, the attestation server 215 communicates with the gateway device 210 and includes a mechanism that prompts the gateway device 210 to prove that it is a particular type of device and has certain characteristics, e.g., RoT, hardware-backed security, software encryption, etc. The attestation mechanism provided may be a software attestation, a hardware attestation or some combination of software attestation and hardware attestation. The gateway device 210 is then assigned a score by the attestation server 215.

Attestation server 215 may determine an identity attestation metric, an attribution metric, a consent/approval metric, a device security level metric and/or a gateway security level metric. A trust score is determined from the scores applied to the plurality of metrics. In one implementation, the attestation server 215 may apply a different weight to certain metrics.

The score for each metric is combined to determine the trust score. The trust score provides an indication that data received from an endpoint device 205 has certain characteristics, e.g., how the data was handled, how the identity was tagged, and/or how the endpoint device proved that it is a certain type of device. This trust score is sent to an analytics server 220 and the analytics server 220 takes an action based on this calculated trust score.

The analytics server 220 can be a health service that determines medical decisions/actions for a patient. As described above, the attestation server 215 communicates with endpoint device 205 and gateway device 210 to determine the trustworthiness of the data from the endpoint device 205. The attestation server 215 determines a trust score and sends the trust score to the analytics server 220. A higher trust score allows the analytics server 220 to determine an action for a patient with greater confidence.

With a higher trust score, i.e., with high data provenance, more comprehensive medical action, e.g., administering a dosage, initiating a therapeutic action, etc., can be automatically initiated by a message sent from the analytics server 220 to drug delivery and/or therapeutic device 225. With a medium trust score, i.e., with mid data provenance, a medical action may include notifying a medical professional, e.g., by automatically sending an alert to monitoring device 230. With a low trust score, i.e., with low data provenance, a medical action may include automatically sending a notification for display to a user of gateway device 210.

In one implementation, the attestation server 215 and the analytics server 220 are cloud-based servers. In one implementation, communications between the endpoint device 205 and the attestation server 215 are passed through gateway device 210.

In one implementation, endpoint device 205 may communicate directly with the attestation server. This communication may be accomplished via WiFi, Ethernet, cellular, or other direct IP addressable networks.

The endpoint device 205 and gateway device 210 employ a sufficient degree of trust such that these devices can safely store credentials and be able to present the credentials to the device that is performing the attestation, e.g., attestation server 215.

In one implementation, trust is built up from a common root that is typically embedded in the hardware at the point of manufacture. This Root of Trust (RoT) is employed in the boot sequences to load the operating system (OS) and all subsequent operations. In general, RoT serves as a separate computing engine that controls a trusted computing platform. Attestation server 215 can leverage this trusted computing platform to affirm that the device, including hardware and software, has not been tampered with and is genuine.

In the event that no attestation service is available on an endpoint device or gateway, an attestation procedure may return (NULL/0) on the endpoint device or gateway being attested. For example, the lowest level of Bluetooth attestation is a standard Bluetooth Low Energy (BLE) advertisement. Many current BLE consumer medical devices do not include RoT or any kind of formal attestation mechanism. The lack of a formal attestation mechanism for an endpoint or gateway device results in a lower trust score for data sent from or through these devices.

Figure 3:
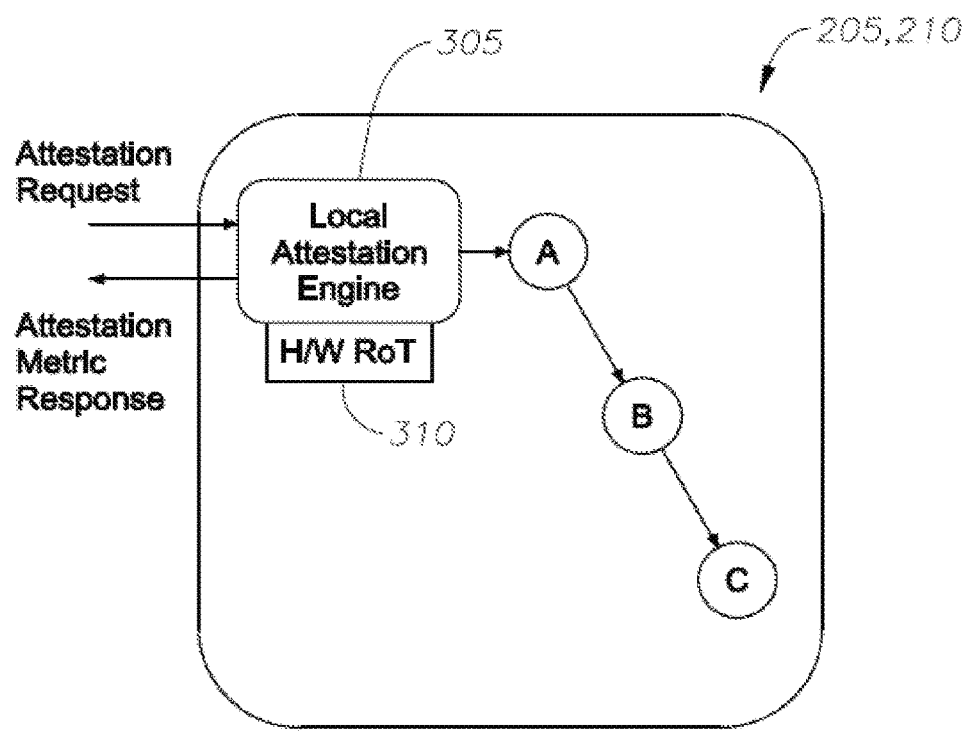
FIG. 3 illustrates a dependency path for an attestation evaluation in accordance with implementations of various techniques described herein.
Figure 4:
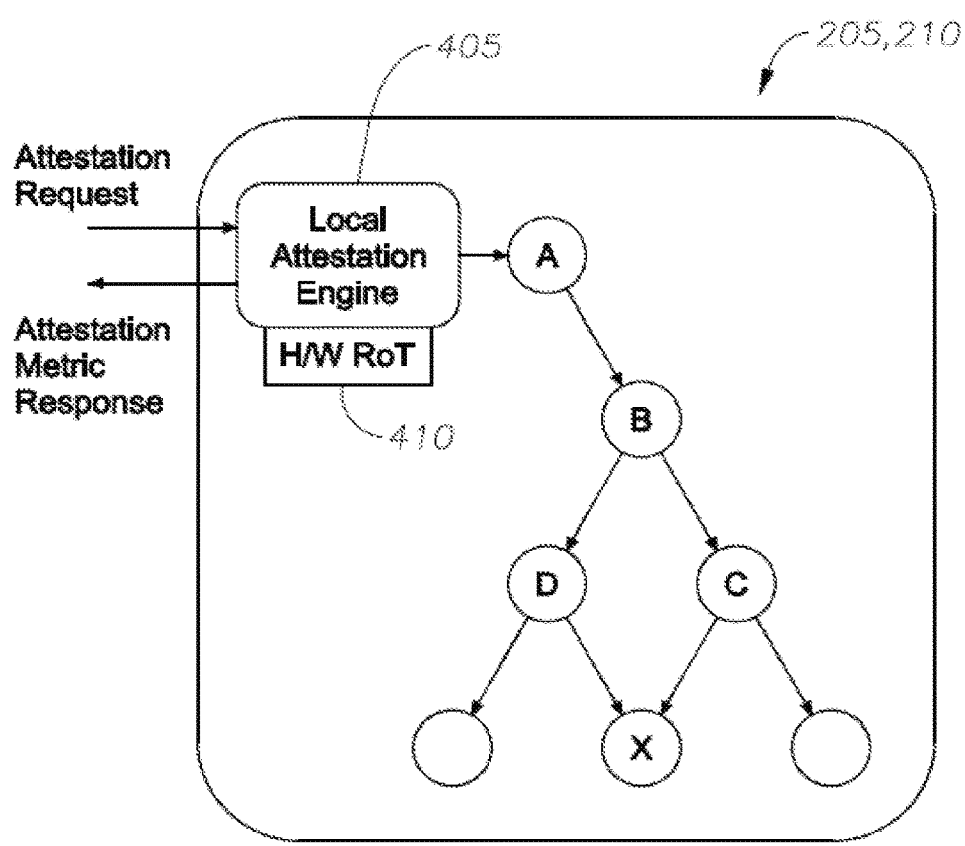
FIG. 4 illustrates a dependency path for an attestation evaluation in accordance with implementations of various techniques described herein.

The attestation process can be leveraged to ensure that the data processing pipeline remains unaltered or without interference. FIG. 3 and FIG. 4 illustrate dependency paths for an attestation evaluation. As the attestation evaluation traverses the dependency paths, the evaluation patterns will either resemble a linear evaluation, as shown in FIG. 3, or a graph evaluation, as shown in FIG. 4, where common nodes may be present. Although FIG. 3 and FIG. 4 describe the dependency paths as including components or applications, the elements of each dependency path may include any item, e.g., software, hardware, or any combination of software and hardware, capable of validation by attestation.

In one implementation, when a device, e.g., endpoint device 205 or gateway device 210, is remotely attested, an attestation request received from attestation server 215 is issued to a local attestation engine. In one implementation, the local attestation engine employs RoT. When RoT is employed, the local attestation engine validates the hardware and evaluates the application(s).

FIG. 3 illustrates a linear scenario of an evaluation of trust by a local attestation engine 305 of a device 205, 210. Each device 205, 210 may include a hardware RoT 310. In FIG. 3, the application A depends on a component B which depends on a component C. In this scenario, the chain A→B→C is validated.

FIG. 4 illustrates a common node scenario of an evaluation of trust by a local attestation engine 405 of a device 205, 210. Each device 205, 210 may include a hardware RoT 410. In FIG. 4, the application A depends on component B which in turn depends on component C and component D. As a part of the evaluation, dependencies of component C and component D are also evaluated. In this scenario, component X (which can be any hardware or software component of device 205, 210 such as a driver or Bluetooth Low Energy (BLE) module), is evaluated once and the attestation information for this component is stored by the local attestation engine 405. Since component X is a common node, when a subsequent request for evaluation that has a dependency chain that includes component X is received, the previously stored attestation information for component X can be retrieved by the local attestation engine 405. Providing attestation in this manner optimizes the attestation process and allows the attestation of component dependencies to be performed in a more efficient manner. Once all paths are evaluated, the attestation metric response is securely communicated outbound to the attestation server 215.

Another example includes a scenario where gateway 210 receives an attestation request from attestation server 215. Based on the attestation request, the device attests the hardware and software of the device. Gateway 210 determines different drivers that are to be attested. In addition, gateway 210 is receiving two different data types from two different endpoint devices. For instance, gateway 210 receives oxygen readings of a patient from a first endpoint device and blood pressure readings of the patient from a second endpoint device. The first endpoint device depends on a Bluetooth stack. An attestation is performed on the Bluetooth stack of the gateway device 210. The second endpoint device also depends on a Bluetooth stack. Since the Bluetooth stack of the gateway device 210 has already been evaluated and attested, the Bluetooth stack of the gateway device 210 does not need to be evaluated again. In the same device there can be multiple paths for different endpoint devices and/or channels of data.

Figure 5:
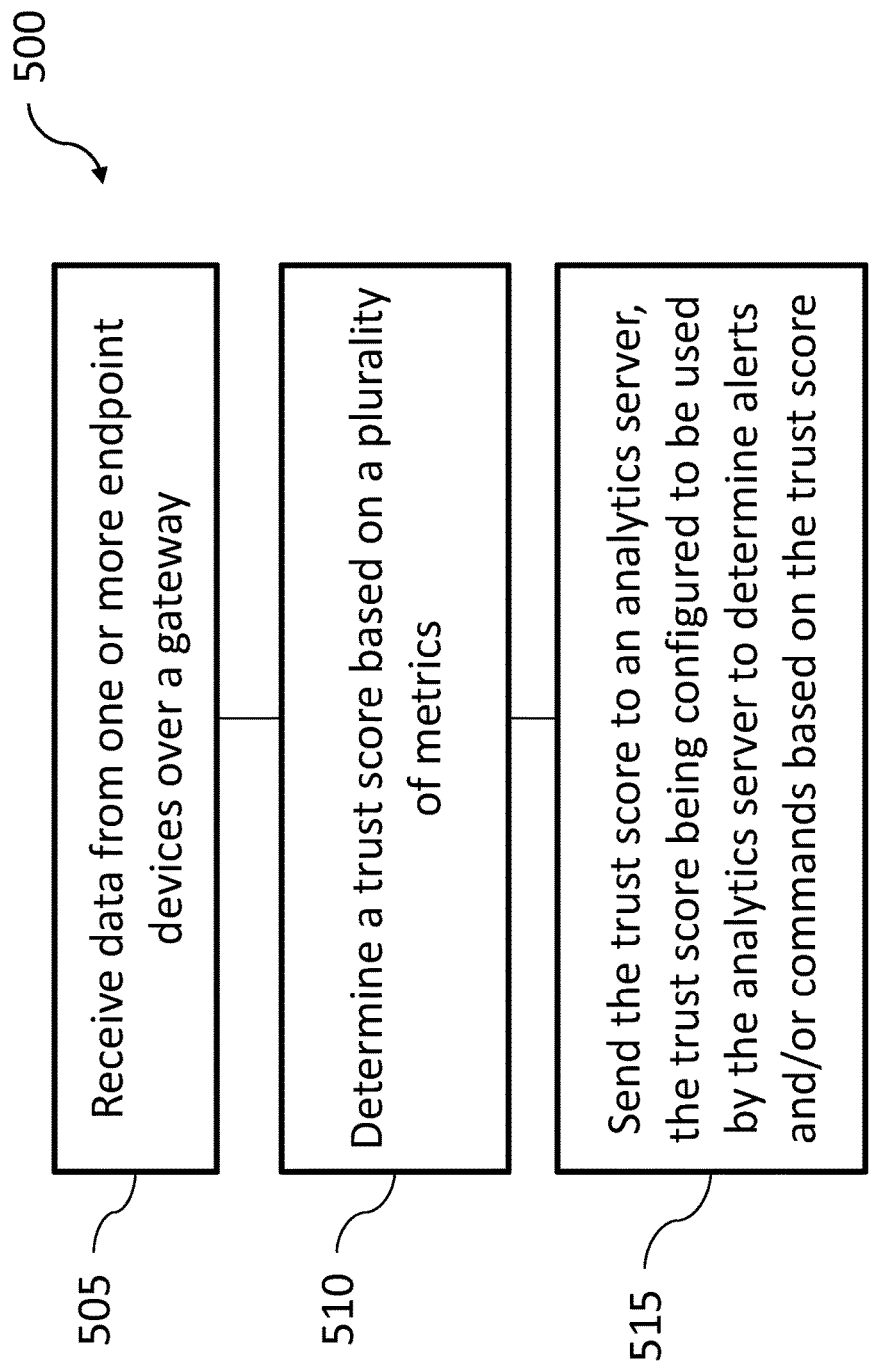
FIG. 5 illustrates a block diagram of a method for determining a trust score in accordance with implementations of various techniques described herein.

FIG. 5 illustrates a block diagram of a method for determining a trust score. At block 505, data is received from one or more endpoint devices, e.g., endpoint device 205, over a gateway, e.g., gateway device 210.

In one implementation, each of the one or more endpoint devices may include a RoT engine. In another implementation the gateway may include a RoT engine.

In one implementation, the gateway and each of the one or more endpoint devices may include a RoT engine. In one implementation, the one or more endpoint devices and the gateway are part of a TEE.

At block 510, a trust score is determined based on a plurality of metrics. The plurality of metrics may include, but are not limited to: device attestation, gateway attestation, identity attestation, attribution, consent/approval, device security level, and gateway security level. A subject, e.g., device, data path, software, software code section, protocol, of each metric is designated points within the metric based on a level of security provided by the subject. In one implementation, weights can be assigned to each metric to provide a weighted trust score.

At block 515, the trust score is sent to an analytics server, e.g., analytics server 220. The trust score is configured to be used by the analytics server to determine alerts and/or commands based on the trust score. Determining an alert and/or command may include initiating a medical action, e.g., delivering a dosage to a patient in a high data provenance scenario. Determining an alert and/or command may also include delivering a notification to a medical professional in a mid data provenance scenario. Determining an alert and/or command may further include sending a notification to a user of a gateway device in a low data provenance scenario.

Figure 6:
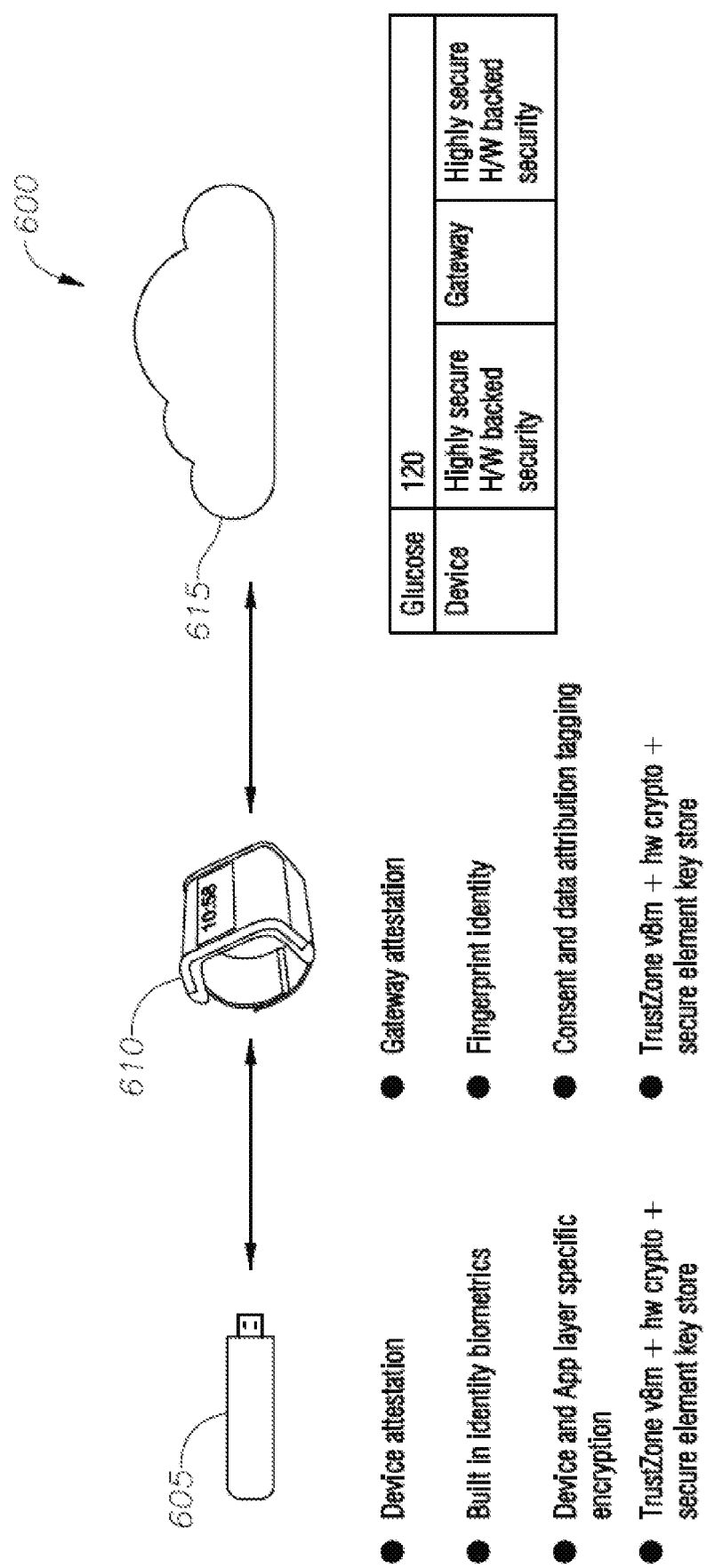
FIG. 6 illustrates a diagram of a high data provenance system in accordance with implementations of various techniques described herein.
Figure 8:
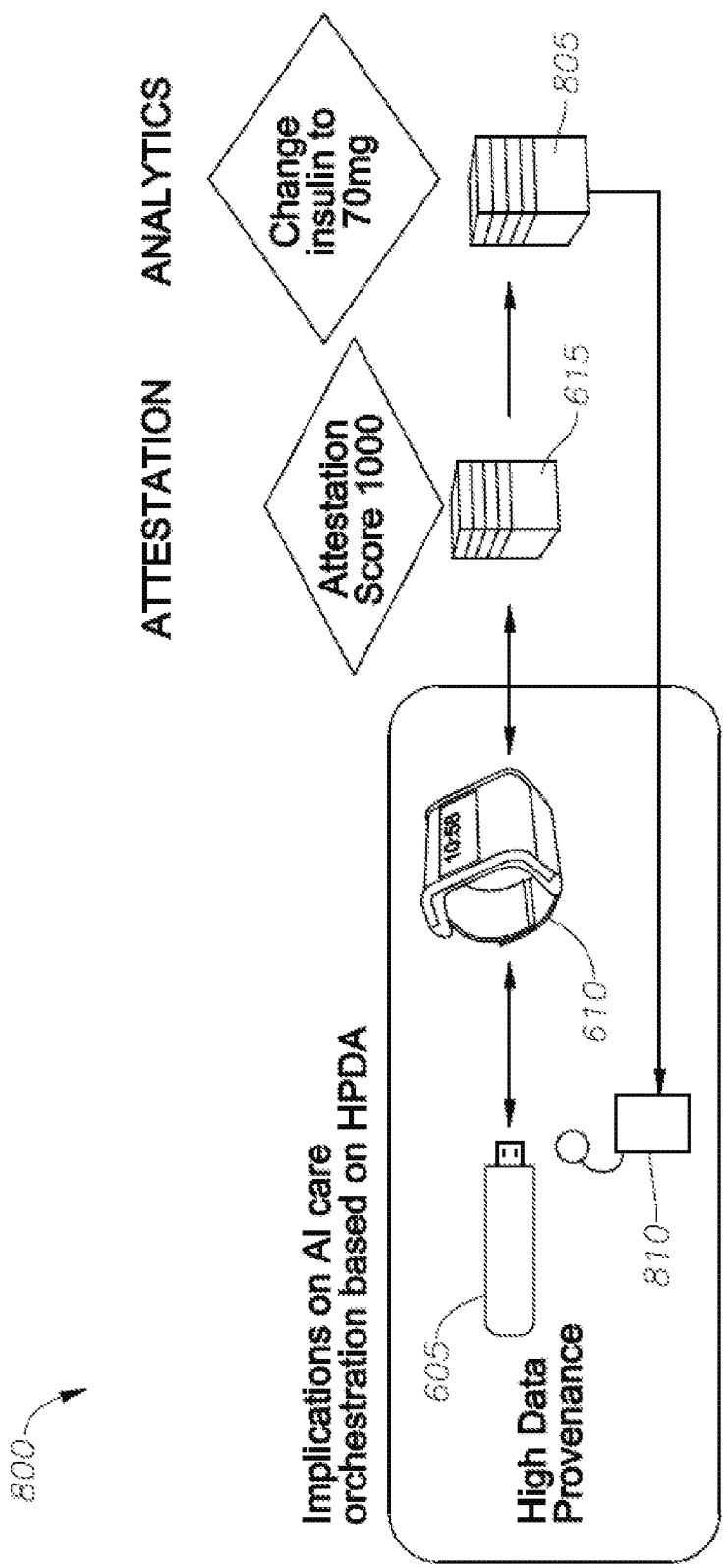
FIG. 8 illustrates a diagram of a high data provenance system in accordance with implementations of various techniques described herein.

FIGS. 6-8 illustrate an example of a high data provenance scenario. FIG. 6 illustrates a diagram of a high data provenance system 600 that includes an endpoint device 605, a gateway device 610, and an attestation server 615. In this example, endpoint device 605 is a glucose meter and gateway device 610 is a smart watch. The security features included in endpoint device 605 are: device attestation, built-in identity biometrics, device and application layer specific encryption and a TEE that includes hardware cryptography and a secure element key store. The security features included in gateway device 610 are: gateway attestation, fingerprint identity, consent and data attribution tagging, and a TEE that includes hardware cryptography and a secure element key store. As a result, the glucose reading of 120 is being sent over an endpoint device 605 and a gateway 610 having highly-secure hardware backed security.

FIG. 7 illustrates a table 700 that includes the plurality of metrics used to determine a trust score for system 600. The plurality of metrics includes device attestation, gateway attestation, identity attestation, attribution, consent/approval, device security level and gateway security level. Each metric is assigned a weight. In this example, device attestation, gateway attestation and consent/approval are assigned a weight of '2' and identity attestation, attribution, device security level and gateway security level are assigned a weight of '1.' Based on the security features described in FIG. 6, points are determined for each of the plurality of metrics. In this example, a point level of 100 was determined for each of the plurality of metrics. Multiplying the weight formula by the number of points for each metric provides a score for each metric. The scores for each metric are then added to determine a total score, e.g., trust score. In this example, the trust score is 1000.

Accordingly, since the trust score for the data received from endpoint device 605 is high, it may be considered appropriate to respond to the received data with a high level of invasiveness or risk to the patient. FIG. 8 includes a diagram of a high data provenance system including endpoint device 605, gateway device 610, attestation server 615, analytics server 805 and drug delivery device 810. As illustrated in the FIG. 8, the glucose reading of 120 from endpoint device 605 is sent to attestation server 615 through gateway device 610. The attestation server 615 determines the trust score and sends the glucose reading along with the trust score to analytics server 805. Based on the trust score exhibiting high data provenance and on the received glucose information data, the analytics server 805 makes a determination to deliver insulin to the patient, e.g., using drug delivery device 810. This action by the analytics server 805 could create a risk to the patent if the data was incorrect, however, since the data is trusted, the insulin can be delivered at a lower risk to the patient.

Figure 9:
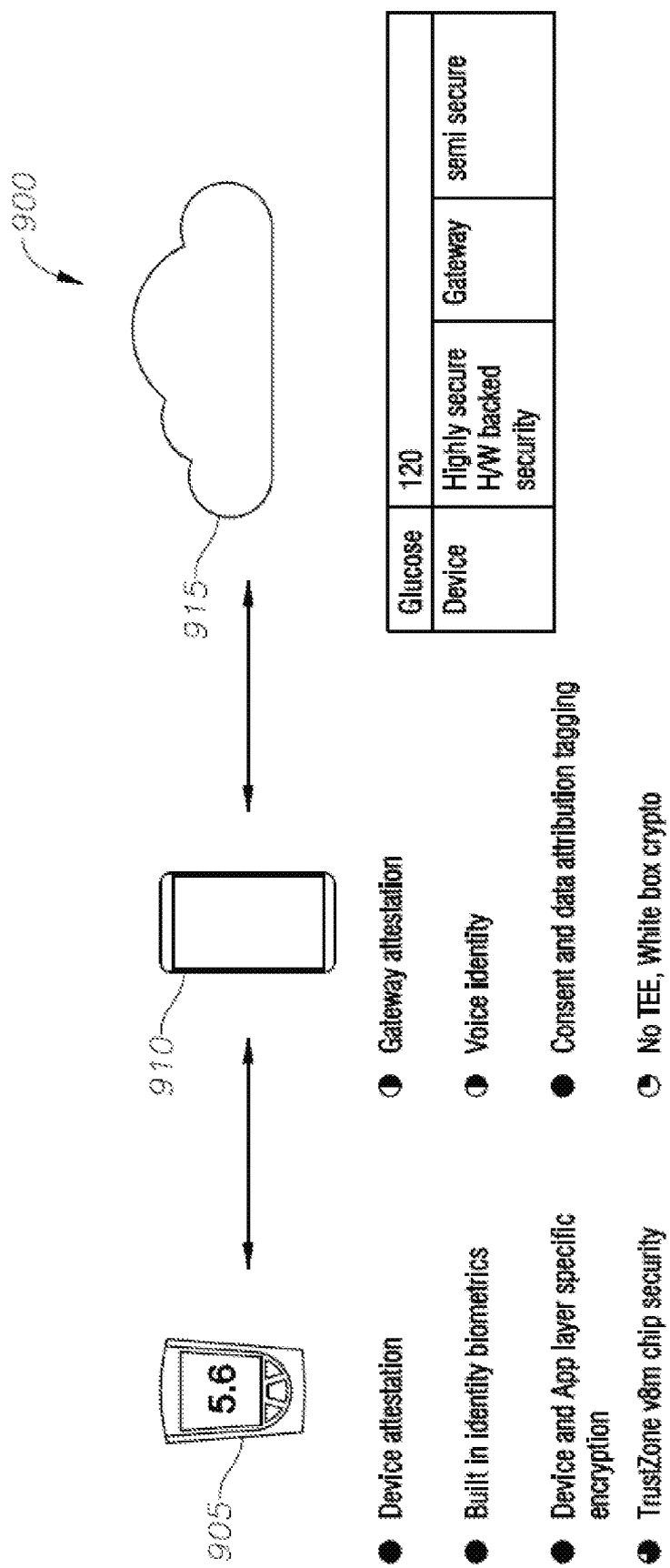
FIG. 9 illustrates a diagram of a mid data provenance system in accordance with implementations of various techniques described herein.
Figure 11:
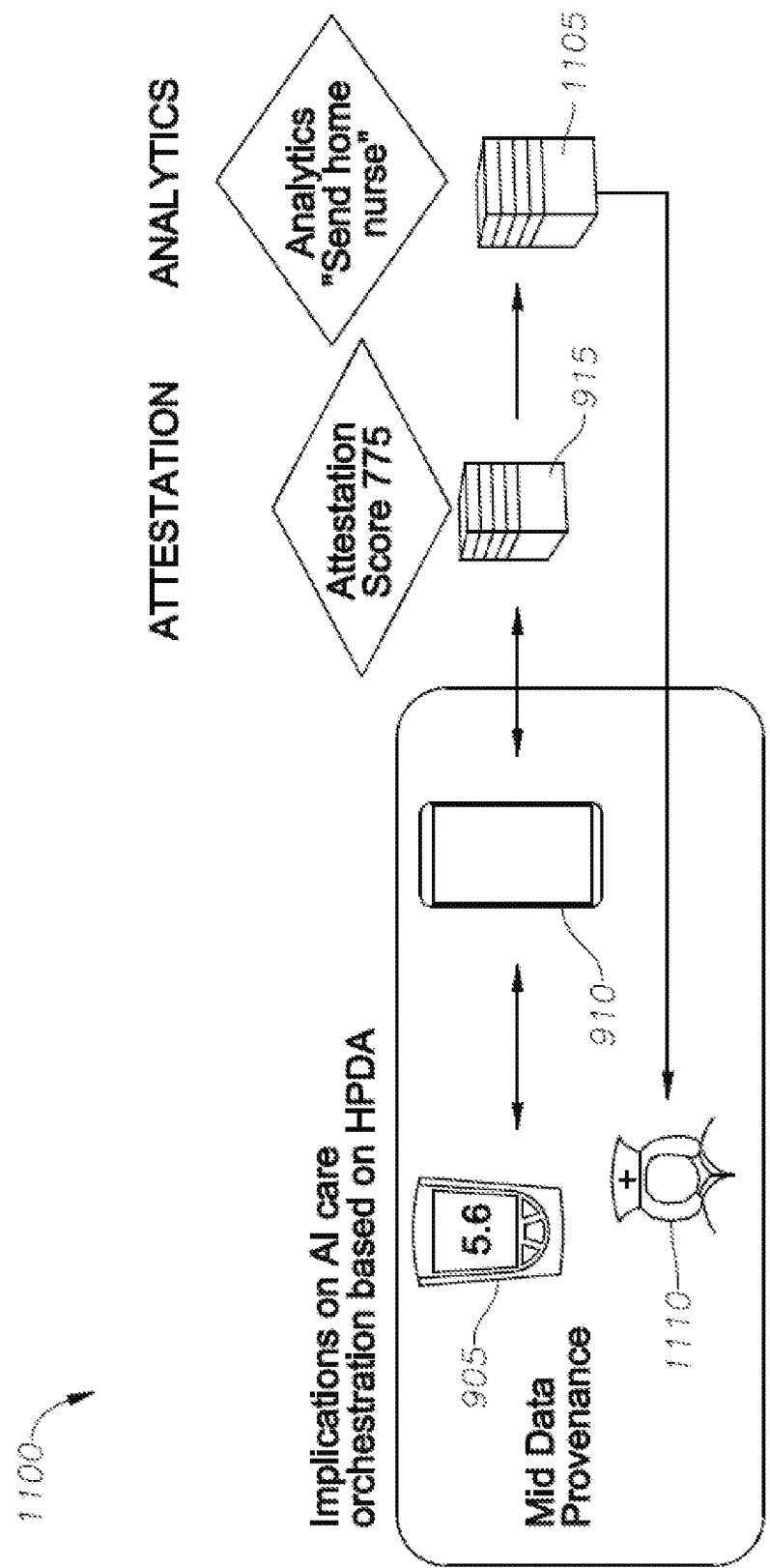
FIG. 11 illustrates a diagram of a mid data provenance system in accordance with implementations of various techniques described herein.

FIGS. 9-11 illustrate an example of a mid-data provenance scenario. FIG. 9 illustrates a diagram of a system 900 that includes an endpoint device 905, a gateway device 910, and an attestation server 915. In this example, endpoint device 905 is a glucose meter and gateway device 910 is a smart phone. The security features included in endpoint device 905 are: device attestation, built-in identity biometrics, device and application layer specific encryption and partial TEE security. The security features included in gateway device 910 are: partial gateway attestation, voice identity, consent and data attribution tagging, and white box cryptography. As a result, the glucose reading of 120 is being sent over an endpoint device 905 having highly-secure hardware backed security and a gateway 910 having semi-secure security features.

FIG. 10 illustrates an example table 1000 that includes the plurality of metrics used to determine a trust score for system 900. The plurality of metrics includes device attestation, gateway attestation, identity attestation, attribution, consent/approval, device security level and gateway security level. Each metric is assigned a weight. In this example, device attestation, gateway attestation and consent/approval are assigned a weight of '2' and identity attestation, attribution, device security level and gateway security level are assigned a weight of '1.' Based on the security features described in FIG. 9, points are determined for each of the plurality of metrics. In this example, a point level of 75 was determined for the device attestation, gateway attestation, identity attestation, consent/approval, device security level, and gateway security level metrics. A point level of 100 was determined for the attribution metric. Multiplying the weight formula by the number of points for each metric provides a score for each metric. The scores for each metric are then added to determine a total score, e.g., trust score. In this example, the trust score is 775.

In this example, the trust score is at a level below the highest value. There are a number of reasons that factor into a lower trust score, such as: (i) the gateway through which the data travels (e.g. user's smartphone) is less trusted or there is no end-to-end security (which might allow intermediate parties to modify the data), or (ii) the device has less hardware security capabilities. As such, a medium level of trust is established in the same data as the high level of trust example above in FIGS. 6-8. As described in FIG. 11, based on the same data a cloud-based analytics server may elect to trigger a different action based on the lower trust score. For example, the service may elect to take a less risky/invasive action such as notifying a care provider.

FIG. 11 includes a diagram of a mid data provenance system 1100 including endpoint device 905, gateway device 910, attestation server 915, analytics server 1105 and monitoring device 1110. As illustrated in the FIG. 9, the glucose reading of endpoint device 905 is sent to attestation server 915 through gateway device 910. The attestation server 915 determines the trust score and sends the glucose reading along with the trust score to analytics server 1105. Based on the trust score exhibiting mid data provenance and on the received glucose information data, the analytics server makes a determination to notify a care provider, e.g., using monitoring device 1110.

Figure 12:
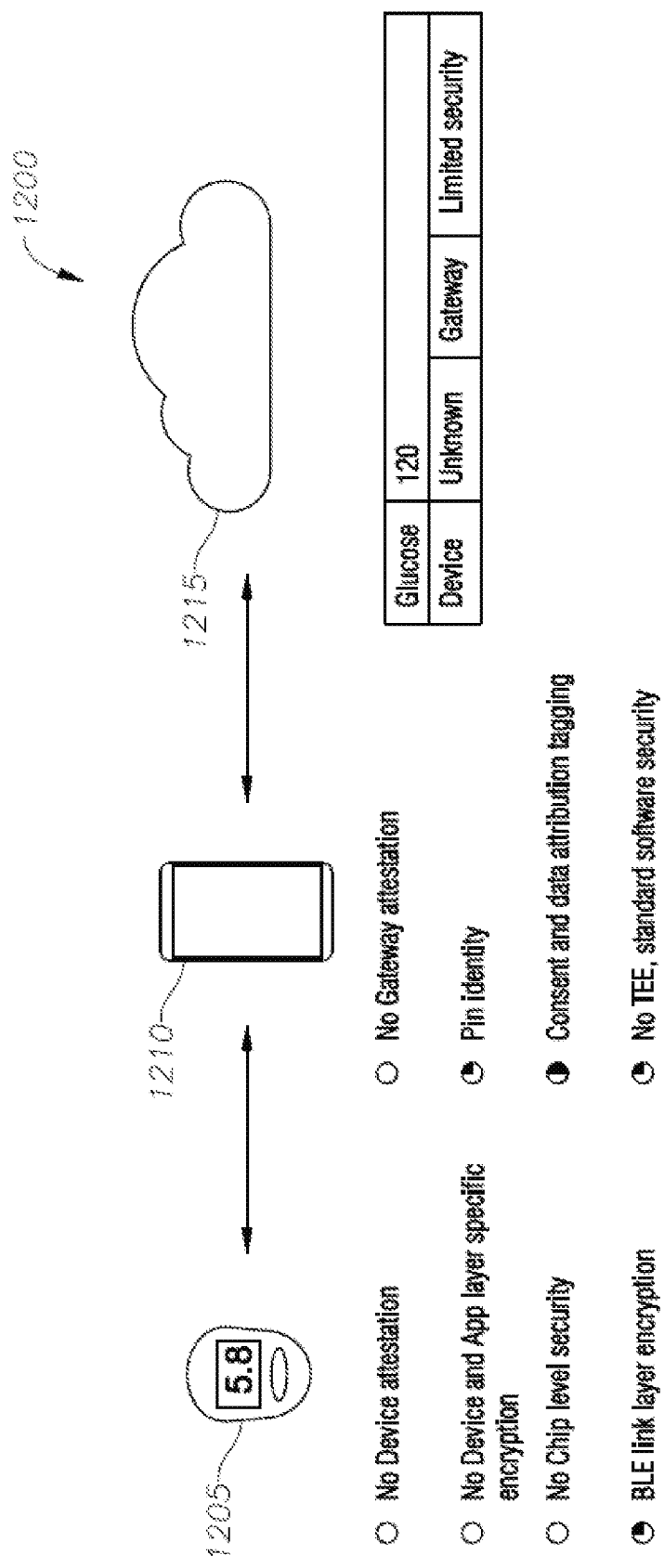
FIG. 12 illustrates a diagram of a low data provenance system in accordance with implementations of various techniques described herein.
Figure 14:
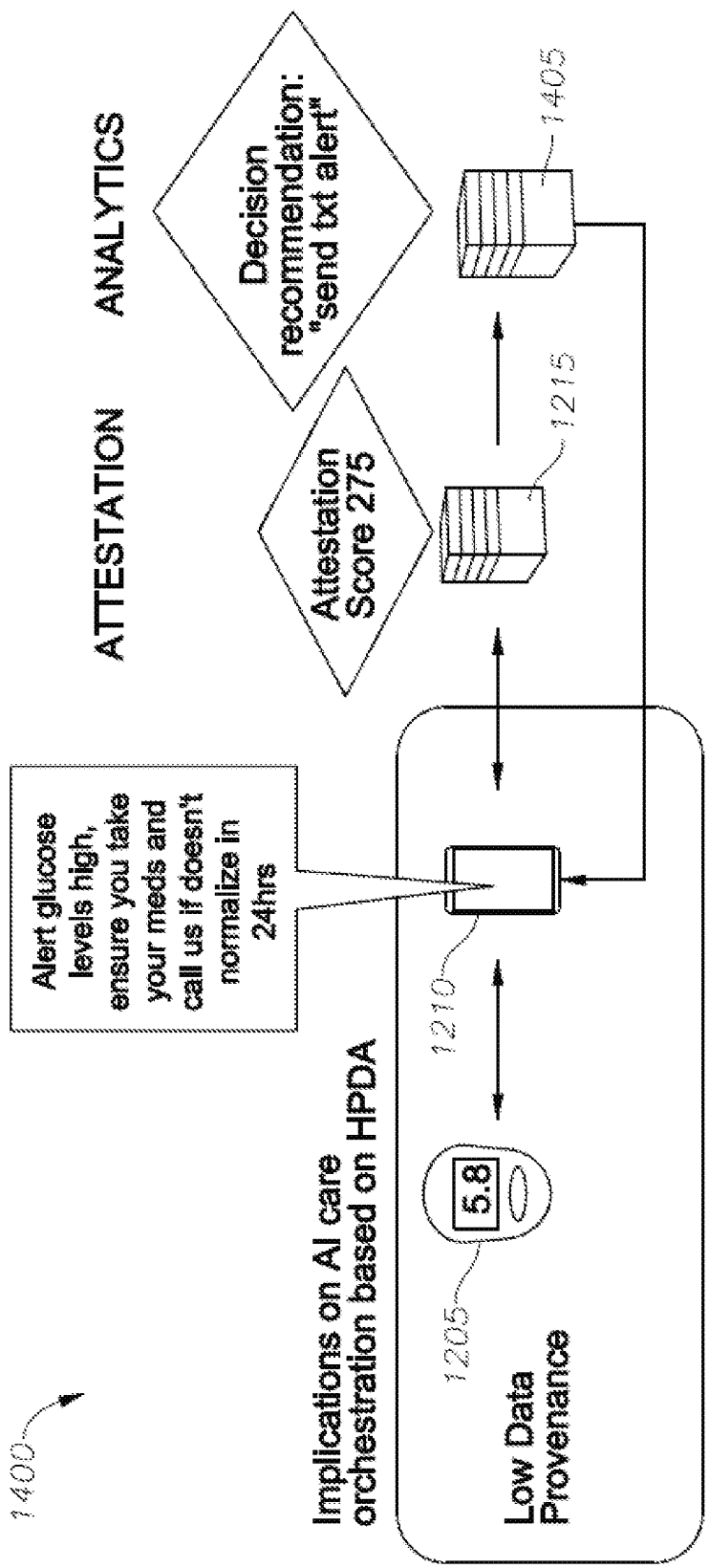
FIG. 14 illustrates a diagram of a low data provenance system in accordance with implementations of various techniques described herein.

FIGS. 12-14 illustrate an example low data provenance scenario. FIG. 12 illustrates a diagram of a system 1200 that includes an endpoint device 1205, a gateway device 1210, and an attestation server 1215. In this example, endpoint device 1205 is a glucose meter and gateway device 1210 is a smart phone. The endpoint device 1205 does not include device attestation, device and application layer specific encryption or chip level security. The only security feature for endpoint device 1205 is Bluetooth Low Energy (BLE) layer encryption. The gateway device 1210 does not include gateway attestation. However, the gateway device 1210 does include the following security features: personal identification number (PIN) identity, partial consent and data attribution tagging, and standard software security. As a result, the glucose reading of 120 is being sent over endpoint device 1205 having unknown security and a gateway 1210 having limited security features.

FIG. 13 illustrates an example table 1300 that includes the plurality of metrics used to determine a trust score for system 1200. The plurality of metrics includes device attestation, gateway attestation, identity attestation, attribution, consent/approval, device security level and gateway security level. Each metric is assigned a weight. In this example, device attestation, gateway attestation and consent/approval are assigned a weight of '2' and identity attestation, attribution, device security level and gateway security level are assigned a weight of '1.' Based on the security features described in FIG. 12, points are determined for each of the plurality of metrics. In this example, a point level of 0 was determined for the device attestation, gateway attestation and device security level metrics. A point level of 50 was determined for the identity attestation, attribution and consent/approval metrics. A point level of 25 was determined for the gateway security level metric. Multiplying the weight formula by the number of points for each metric provides a score for each metric. The scores for each metric are then added to determine a total score, e.g., trust score. In this example, the trust score is 275.

In this example, the trust score is at a low level. There are a number of reasons that factor into the low trust score, such as: (i) low encryption or security capabilities on the device, (ii) no or low-security user validation of the data, and (iii) limited security on the gateway route through which the data was provided to the to an attestation server. As such, a low level of trust is established in the same data as the high and mid level of trust examples above in FIGS. 6-11. As described in FIG. 14, based on the same data, a cloud-based analytics server may elect to trigger a different action based on the low trust score. For example, the service may elect to take an even lower risk action such as sending a notification to the user's smartphone.

FIG. 14 includes a diagram of a low data provenance system 1400 including endpoint device 1205, gateway device 1210, attestation server 1215, and analytics server 1405. As illustrated in the FIG. 14, the glucose reading of endpoint device 1205 is sent to attestation server 1215 through gateway device 1210. The attestation server 1215 determines the trust score and sends the glucose reading along with the trust score to analytics server 1405. Based on the trust score exhibiting low data provenance and on the received glucose information data, the analytics server makes a determination to send a notification to a user's smart phone, e.g., gateway device 1210.

Determining a trust score using an attestation server allows an analytics server to generate a response to received data. Based on the trust score, the generated response to the received data is determined in a manner that is appropriate for the level of trust in the received data.

Figure 15:
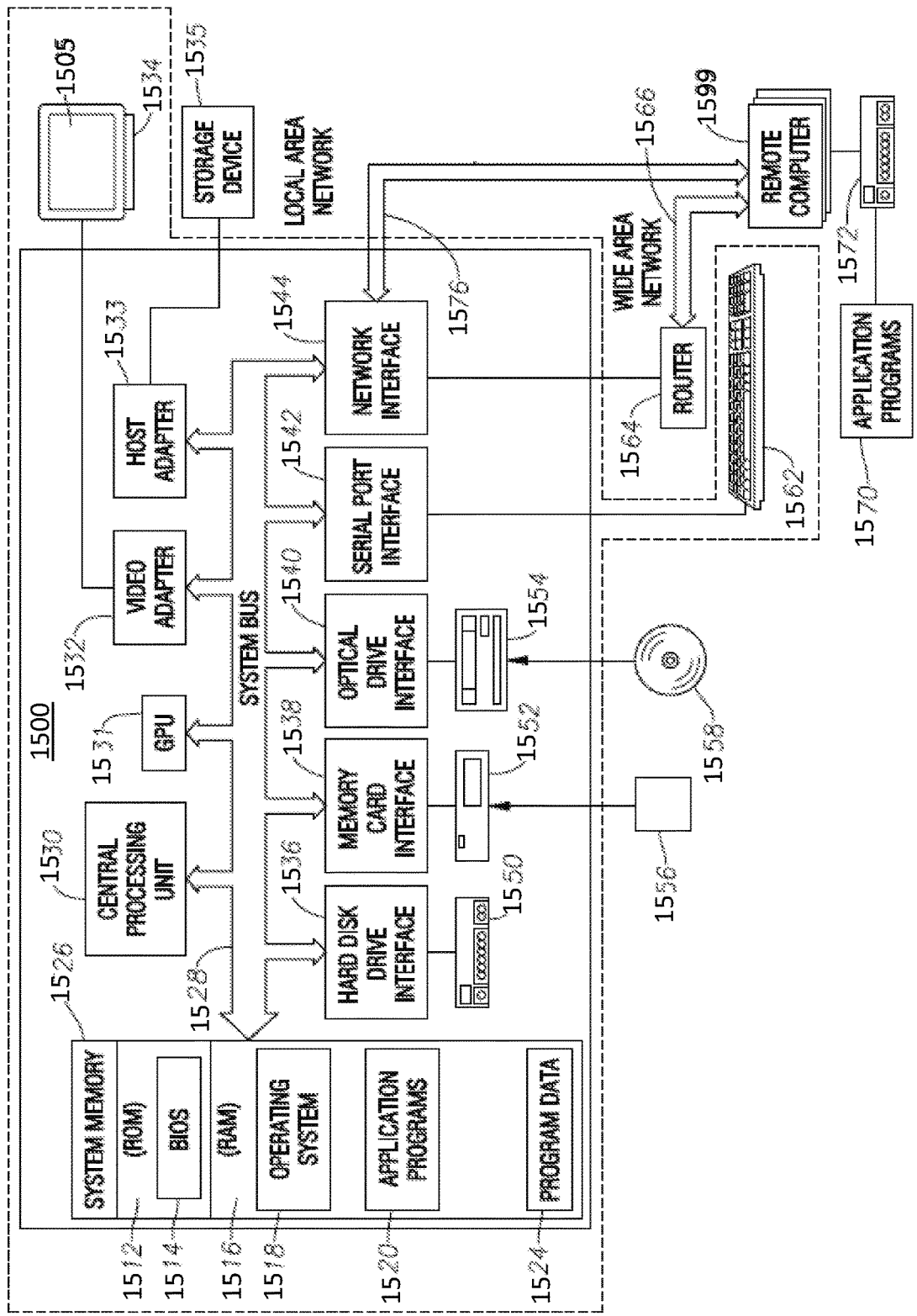
FIG. 15 illustrates a computer system for determining a trust score in accordance with implementations of various techniques described herein.

FIG. 15 illustrates a computing system 1500 in accordance with implementations of various techniques described herein. The computing system 1500 may include a central processing unit (CPU) 1530, a system memory 1526, a graphics processing unit (GPU) 1531 and a system bus 1528 that couples various system components including the system memory 1526 to the CPU 1530. Although only one CPU 1530 is illustrated in FIG. 15, it should be understood that in some implementations the computing system 1500 may include more than one CPU 1530.

The CPU 1530 may include a microprocessor, a microcontroller, a processor, a programmable integrated circuit, or a combination thereof. The CPU 1530 can comprise an off-the-shelf processor such as a Reduced Instruction Set Computer (RISC), or a Microprocessor without Interlocked Pipeline Stages (MIPS) processor, or a combination thereof. The CPU 1530 may also include a proprietary processor.

The GPU 1531 may be a microprocessor specifically designed to manipulate and implement computer graphics. The CPU 1530 may offload work to the GPU 1531. The GPU 1531 may have its own graphics memory, and/or may have access to a portion of the system memory 1526. As with the CPU 1530, the GPU 1531 may include one or more processing units, and each processing unit may include one or more cores.

The CPU 1530 may provide output data to a GPU 1531. The GPU 1531 may generate graphical user interfaces that present the output data. The GPU 1531 may also provide objects, such as menus, in the graphical user interface. A user may provide inputs by interacting with the objects. The GPU 1531 may receive the inputs from interaction with the objects and provide the inputs to the CPU 1530. A video adapter 1532 may be provided to convert graphical data into signals for a monitor 1534. The monitor 1534 includes a screen 1505. In certain implementations, the screen 1505 may be sensitive to touching by a finger. In other implementations, the screen 1505 may be sensitive to the body heat from the finger, a stylus, or responsive to a mouse. Additionally, in certain implementations, the screen may have the capability of displaying more than one plan position indicator (PPI).

The system bus 1528 may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 1526 may include a read only memory (ROM) 1512 and a random access memory (RAM) 1516. A basic input/output system (BIOS) 1514, containing the basic routines that help transfer information between elements within the computing system 1500, such as during start-up, may be stored in the ROM 1512.

The computing system 1500 may further include a hard disk drive interface 1536 for reading from and writing to a hard disk 1550, a memory card reader 1552 for reading from and writing to a removable memory card 1556, and an optical disk drive 1554 for reading from and writing to a removable optical disk 1558, such as a CD ROM or other optical media. The hard disk 1550, the memory card reader 1552, and the optical disk drive 1554 may be connected to the system bus 1528 by a hard disk drive interface 1536, a memory card reader interface 1538, and an optical drive interface 1540, respectively. The drives and their associated computer-readable media may provide nonvolatile storage of computer-readable instructions, data structures, program modules and other data for the computing system 1500.

Although the computing system 1500 is described herein as having a hard disk, a removable memory card 1556 and a removable optical disk 1558, it should be appreciated by those skilled in the art that the computing system 1500 may also include other types of computer-readable media that may be accessed by a computer. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the computing system 1500. Communication media may embody computer readable instructions, data structures, program modules or other data in a modulated data signal, such as a carrier wave or other transport mechanism and may include any information delivery media. The term "modulated data signal" may mean a signal that has one or more of its characteristics set or changed in such a manner as to encode information in the signal. By way of example, and not limitation, communication media may include wired media such as a wired network or direct-wired connection, and wireless media such as acoustic, RF, infrared and other wireless media. The computing system 1500 may also include a host adapter 1533 that connects to a storage device 1535 via a small computer system interface (SCSI) bus, a Fiber Channel bus, an eSATA bus, or using any other applicable computer bus interface.

The computing system 1500 can also be connected to a router 1564 to establish a wide area network (WAN) 1566 with one or more remote computers 1599. The router 1564 may be connected to the system bus 1528 via a network interface 1544. The remote computers 1599 can also include hard disks 1572 that store application programs 1570.

In another implementation, the computing system 1500 may also connect to the remote computers 1599 via local area network (LAN) 1576 or the WAN 1566. When using a LAN networking environment, the computing system 1500 may be connected to the LAN 1576 through the network interface or adapter 1544. The LAN 1576 may be implemented via a wired connection or a wireless connection. The LAN 1576 may be implemented using Wi-Fi™ technology, cellular technology, Bluetooth™ technology, satellite technology, or any other implementation known to those skilled in the art. The network interface 1544 may also utilize remote access technologies (e.g., Remote Access Service (RAS), Virtual Private Networking (VPN), Secure Socket Layer (SSL), Layer 6 Tunneling (L2T), or any other suitable protocol). These remote access technologies may be implemented in connection with the remote computers 1599. It will be appreciated that the network connections shown are exemplary and other means of establishing a communications link between the computer systems may be used.

A number of program modules may be stored on the hard disk 1550, memory card 1556, optical disk 1558, ROM 1512 or RAM 1516, including an operating system 1518, one or more application programs 1520, and program data 1524. In certain implementations, the hard disk 1550 may store a database system. The database system could include, for example, recorded points. The application programs 1520 may include various mobile applications ("apps") and other applications configured to perform various methods and techniques described herein. The operating system 1518 may be any suitable operating system that may control the operation of a networked personal or server computer.

A user may enter commands and information into the computing system 1500 through input devices such as buttons 1562, which may be physical buttons, virtual buttons, or combinations thereof. Other input devices may include a microphone, a mouse, or the like (not shown). These and other input devices may be connected to the CPU 1530 through a serial port interface 1542 coupled to system bus 1528, but may be connected by other interfaces, such as a parallel port, game port or a universal serial bus (USB).

In one implementation, the one or more application programs 1520 or 1570 stored in the computer-readable media can include a plurality of instructions that when executed by a processing unit, such as a CPU 1530, cause the computing system to perform any of the techniques, or portions thereof, that are described herein.

Described herein are implementations of various technologies for determining a multi-factor trust score. Data from one or more endpoint devices is received over a gateway. A trust score is determined based on a plurality of metrics. The plurality of metrics including at least: a first attestation process performed for the one or more endpoint devices, and a second attestation process performed for the gateway. The trust score is sent to an analytics server. The trust score is configured to be used by the analytics server to determine an alert and/or a command based on the trust score.

Described herein is also a cloud-based attestation server including a computer system having a processor and memory having stored thereon a plurality of executable instructions which, when executed by the processor, cause the processor to: receive data from one or more endpoint devices over a gateway; determine a trust score based on a plurality of metrics, the plurality of metrics including at least: a first attestation process performed for the one or more endpoint devices, and a second attestation process performed for the gateway; and send the trust score to an analytics server, the trust score configured to be used by the analytics server to determine an alert and/or a command based on the trust score.

In one implementation, the plurality of metrics further include a third attestation process based on an authentication status of an identity of an entity participating in an acquisition and/or handling of the data. The plurality of metrics may further include at least one of an attribution metric, a consent and/or approval metric, a device security level metric, and a gateway security level metric.

In one implementation, each of the one or more endpoint devices may include a root of trust computing engine.

In one implementation, the gateway may include a root of trust computing engine.

In one implementation, the gateway and each of the one or more endpoint devices may include a root of trust computing engine. The one or more endpoint devices and the gateway may be part of a trusted execution environment.

In one implementation, a score can be determined for each of the plurality of metrics. In one implementation, the score for each of the plurality of metrics may be combined to determine the trust score.

In one implementation, a weight may be applied to each of the plurality of metrics. The weight for each of the plurality of metrics may be applied to the score that is determined for each of the plurality of metrics to determine a weighted score for each of the plurality of metrics. The weighted score for each of the plurality of metrics may be combined to determine the trust score.

In one implementation, determining the command may include automatically initiating a medical action. The medical action may include automatically delivering a dosage.

In one implementation, determining the alert may include automatically delivering a notification to a medical professional.

In one implementation, determining the alert may include sending a notification to the gateway. The discussion of the present disclosure is directed to certain specific implementations. It should be understood that the discussion of the present disclosure is provided for the purpose of enabling a person with ordinary skill in the art to make and use any subject matter defined herein by the subject matter of the claims.

It should be intended that the subject matter of the claims not be limited to the implementations and illustrations provided herein, but include modified forms of those implementations including portions of the implementations and combinations of elements of different implementations within the scope of the claims. It should be appreciated that in the development of any such implementation, as in any engineering or design project, numerous implementation-specific decisions should be made to achieve a developers' specific goals, such as compliance with system-related and business related constraints, which may vary from one implementation to another. Moreover, it should be appreciated that such a development effort maybe complex and time consuming, but would nevertheless be a routine undertaking of design, fabrication, and manufacture for those of ordinary skill having benefit of this disclosure. Nothing in this application should be considered critical or essential to the claimed subject matter unless explicitly indicated as being "critical" or "essential."

Reference has been made in detail to various implementations, examples of which are illustrated in the accompanying drawings and figures. In the following detailed description, numerous specific details are set forth to provide a thorough understanding of the present disclosure. However, the present disclosure may be practiced without these specific details. In other instances, well-known methods, procedures, components, circuits and networks have not been described in detail so as not to unnecessarily obscure aspects of the embodiments.

It should also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the present disclosure herein is for the purpose of describing particular implementations and is not intended to limit the present disclosure. As used in the description of the present disclosure and appended claims, the singular forms "a," "an," and "the" are intended to include the plural forms as well, unless the context clearly indicates otherwise. The term "and/or" as used herein refers to and encompasses any and all possible combinations of one or more of the associated listed items. The terms "includes," "including," "comprises," and/or "comprising," when used in this specification, specify a presence of stated features, integers, steps, operations, elements, and/or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. As used herein, the terms "up" and "down"; "upper" and "lower"; "upwardly" and "downwardly"; "below" and "above"; and other similar terms indicating relative positions above or below a given point or element may be used in connection with some implementations of various technologies described herein.

While the foregoing is directed to implementations of various techniques described herein, other and further implementations may be devised without departing from the basic scope thereof, which may be determined by the claims that follow.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method, comprising:
 receiving, by an attestation server, data from one or more endpoint devices over a gateway;
 communicating, by the attestation server, to the one or more endpoint devices to receive characteristics of the one or more endpoint devices;
 communicating, by the attestation server, to the gateway to receive characteristics of the gateway;
 determining, by the attestation server, a trust score based on a plurality of metrics, the plurality of metrics including at least:
  a first attestation process performed based on the characteristics of the one or more endpoint devices, and
  a second attestation process performed based on the characteristics of the gateway; and
 sending the trust score, by the attestation server, to an analytics server, the trust score being configured to be used by the analytics server to evaluate trustworthiness of the data and to determine an alert and/or a command.

2. The method of claim 1, wherein the plurality of metrics further include a third attestation process based on an authentication status of an identity of an entity participating in an acquisition and/or handling of the data.

3. The method of claim 2, wherein the plurality of metrics further includes at least one of an attribution metric, a device security level metric, a gateway security level metric, and a consent and/or approval metric.

4. The method of claim 1, wherein the attestation server directly communicates to the one or more endpoint devices to receive characteristics of the one or more endpoint devices.

5. The method of claim 1, wherein the trust score is compared to a plurality of threshold levels prior to authorizing different automated responses.

6. The method of claim 1, wherein the attestation server and analytics server are cloud-based servers.

7. The method of claim 1, wherein each of the one or more endpoint devices includes a root of trust computing engine.

8. The method of claim 1, wherein the gateway includes a root of trust computing engine.

9. The method of claim 1, wherein the gateway and each of the one or more endpoint devices include a root of trust computing engine.

10. The method of claim 9, wherein the one or more endpoint devices and the gateway are part of a trusted execution environment.

11. The method of claim 1, wherein a score is determined for each of the plurality of metrics.

12. The method of claim 11, wherein the score for each of the plurality of metrics is combined to determine the trust score.

13. The method of claim 11, further comprising applying a weight to each of the plurality of metrics.

14. The method of claim 13, wherein the weight for each of the plurality of metrics is applied to the score that is determined for each of the plurality of metrics to determine a weighted score for each of the plurality of metrics.

15. The method of claim 14, wherein the weighted score for each of the plurality of metrics is combined to determine the trust score.

16. The method of claim 5, wherein the plurality of threshold levels includes a first threshold and a second threshold, and at the trust score above the first threshold, the different automated responses comprise automatically initiating a medical action.

17. The method of claim 16, wherein the medical action comprises automatically delivering a dosage.

18. The method of claim 16, wherein at the trust score below the first threshold and above the second threshold, the different automated responses comprise automatically delivering a notification to a medical professional.

19. The method of claim 18, wherein at the trust score below the second threshold the different automated responses comprise sending a notification to the gateway.

20. A cloud-based attestation server, comprising:
a computer system having a processor and memory having stored thereon a plurality of executable instructions which, when executed by the processor, cause the processor to:
receive, by an attestation server, data from one or more endpoint devices over a gateway;
communicate, by the attestation server, to the one or more endpoint devices to receive characteristics of the one or more endpoint devices;
communicate, by the attestation server, to the gateway to receive characteristics of the gateway;
determine, by the attestation server, a trust score based on a plurality of metrics, the plurality of metrics including at least:
a first attestation process performed based on the characteristics of the one or more endpoint devices, and
a second attestation process performed based on the characteristics of the gateway;
send the trust score, by the attestation server, to an analytics server, the trust score configured to be used by the analytics server to evaluate trustworthiness of the data and to determine an alert and/or a command based on the trust score.

* * * * *